(12) United States Patent
Czaplewski et al.

(10) Patent No.: US 10,301,436 B2
(45) Date of Patent: *May 28, 2019

(54) FLAME-RETARDANT ACONITIC ACID-DERIVED CROSS-LINKERS

(71) Applicant: International Business Machines Corporation, Armonk, NY (US)

(72) Inventors: Sarah K. Czaplewski, Rochester, MN (US); Brandon M. Kobilka, Tucson, AZ (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/611,360

(22) Filed: Jun. 1, 2017

(65) Prior Publication Data
US 2018/0346657 A1 Dec. 6, 2018

(51) Int. Cl.
*C08K 5/521* (2006.01)
*C08K 5/524* (2006.01)
(Continued)

(52) U.S. Cl.
CPC ......... *C08G 81/027* (2013.01); *C08G 18/836* (2013.01); *H05K 1/032* (2013.01);
(Continued)

(58) Field of Classification Search
None
See application file for complete search history.

(56) References Cited

U.S. PATENT DOCUMENTS 2,754,319 A * 7/1956 Johnston ............... C07F 9/4006
106/18.14
2016/0251485 A1 9/2016 Boday et al.

FOREIGN PATENT DOCUMENTS

CN 103965245 A 8/2014
CN 104356361 A 2/2015
GB 1482784 A * 8/1977 ........... H05K 3/0094

OTHER PUBLICATIONS

Mengal et al., "Citric acid based durable and sustainable flame retardant treatment for lyocell fabric," Carbohydrate Polymers, vol. 153, 2016, pp. 78-88, Elsevier. DOI: 10.1016/j.carbpol.2016.07.074.

(Continued)

*Primary Examiner* — Richard A Huhn
(74) *Attorney, Agent, or Firm* — Kelsey M. Skodje

(57) ABSTRACT

A flame-retardant aconitic acid-derived cross-linker, a process for forming a flame-retardant resin, and an article of manufacture comprising a material that contains a flame-retardant aconitic acid-derived cross-linker are disclosed. The flame-retardant aconitic acid-derived cross-linker can have at least two phosphoryl or phosphonyl moieties with allyl functional groups, epoxy functional groups, propylene carbonate functional group, or functionalized thioether substituents. The process for forming the flame-retardant polymer can include forming an aconitic acid derivative, forming a phosphorus-based flame-retardant molecule, and reacting the aconitic acid derivative with the phosphorus-based flame-retardant molecule to form a flame-retardant aconitic acid-derived cross-linker, and binding the cross-linker to a polymer. The aconitic acid derivative can be synthesized from aconitic acid obtained from a bio-based source. Examples of aconitic acid derivatives include carboxysuccinic acid, 2-(hydroxymethyl)-1,4-butenediol, and 2-(hy- (Continued)

droxymethyl)-1,4-butanediol. The article of manufacture can further comprise an electronic component.

17 Claims, 18 Drawing Sheets

(51) Int. Cl.
*C07F 9/02* (2006.01)
*C08G 81/02* (2006.01)
*C08G 18/83* (2006.01)
*H05K 1/03* (2006.01)
C07F 9/113 (2006.01)
C07C 69/007 (2006.01)
C07F 9/141 (2006.01)
C07F 9/09 (2006.01)
C07C 69/003 (2006.01)
C08K 5/00 (2006.01)

(52) U.S. Cl.
CPC .......... *C07C 69/003* (2013.01); *C07C 69/007* (2013.01); *C07F 9/091* (2013.01); *C07F 9/093* (2013.01); *C07F 9/113* (2013.01); *C07F 9/1411* (2013.01); *C07F 9/1412* (2013.01); *C08K 5/0066* (2013.01); *C08K 5/521* (2013.01); *C08K 5/524* (2013.01); *C08L 2201/02* (2013.01); *C08L 2666/84* (2013.01)

(56) References Cited

OTHER PUBLICATIONS

Czaplewski et al., "Flame-Retardant Aconitic Acid-Derived Small Molecules," U.S. Appl. No. 15/611,237, filed Jun. 1, 2017.
Czaplewski et al., "Functionalized Flame-Retardant Aconitic Acid-Derived Molecules," U.S. Appl. No. 15/611,313, filed Jun. 1, 2017.
Czaplewski et al., "Flame-Retardant Aconitic Acid-Derived Monomers" U.S. Appl. No. 15/611,423, filed Jun. 1, 2017.
List of IBM Patents or Patent Applications Treated as Related, Signed Jun. 1, 2017, 2 pages.
"Poly Star UM 55", Poly vinyl chloride / Vinyl Acetate copolymer, Data Sheet, retrieved from kianresin.com, Sep. 2018, 2 pages.
Meyer et al., "The synthesis of citric acid phosphate," Journal of the American Chemical Society, 1959, 81, pp. 2094-2096 (Abstract Only).

\* cited by examiner

302

335  2-Mercaptoethanol

340  Cysteamine HCl 345  3-Mercaptopropionate

FLAME-RETARDANT ACONITIC ACID-DERIVED CROSS-LINKERS

BACKGROUND

The present disclosure relates to bio-renewable flame-retardant compounds and, more specifically, flame-retardant cross-linkers derived from aconitic acid.

Bio-based, sustainable compounds can be used in the syntheses of substances that previously required petroleum-based raw materials. Examples of uses for bio-based compounds include polymers, flame retardants, cross-linkers, etc. There are numerous strategies for efficiently and inexpensively producing bio-based compounds on an industrial scale. Examples of these strategies can be found in fermentation technologies, membrane technologies, and genetic engineering. Aconitic acid (propene-1,2,3-tricarboxylic acid) is one example of a bio-based compound that can have applications as a component of various polymers, resins, and small molecules. Aconitic acid is an intermediate in the citric acid cycle, wherein it is acted upon by the aconitase enzyme. Bio-based materials, such as sugarcane or citric acid, are common sources of aconitic acid.

SUMMARY

Various embodiments are directed to flame-retardant aconitic acid-derived cross-linkers. The flame-retardant aconitic acid-derived cross-linkers can have at least two phosphoryl or phosphonyl moieties with allyl functional groups, epoxy functional groups, propylene carbonate functional groups, or functionalized thioether substituents. The functionalized thioether substituent can be a hydroxyl-functionalized thioether substituent, an amino-functionalized thioether substituent, or a carboxylic acid-functionalized thioether substituent. Additional embodiments are directed to forming a flame-retardant polymer. The polymer can be produced by forming an aconitic acid derivative, forming a phosphorus-based flame-retardant molecule, and reacting the aconitic acid derivative and the phosphorus-based flame-retardant molecule to form a flame-retardant aconitic acid-derived cross-linker. The flame-retardant aconitic acid-derived cross-linker can be further reacted with thiol molecules or a combination of lithium bromide and carbon dioxide to form a flame-retardant aconitic acid-derived cross-linker with functionalized thioether or propylene carbonate functional groups, respectively. The flame-retardant aconitic acid-derived cross-linker can then be reacted with a polymer to form the flame-retardant polymer. The aconitic acid derivative can be carboxysuccinic acid, 2-(hydroxymethyl)-1,4-butenediol, or 2-(hydroxymethyl)-1,4-butanediol. The aconitic acid derivatives can be synthesized from aconitic acid that has been obtained from a bio-based source. The phosphorus-based flame-retardant molecule can be a phosphate-based molecule or a phosphonate-based molecule with at least one allyl or epoxy functional group. Further embodiments are directed to an article of manufacture comprising a material that contains a flame-retardant aconitic acid-derived cross-linker. The material can be a resin, adhesive, or polymer. Examples of polymer materials can include polyurethane, epoxies, polyhydroxyurethane, polycarbonates, polyester, polyacrylates, polyimides, polyamides, polyureas, and poly(vinyl-ester). The article of manufacture can further comprise an electronic component.

DETAILED DESCRIPTION

Bio-based compounds are increasingly being used in the synthesis of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale.

Examples of strategies for producing bio-based compounds can be found in fermentation technologies, membrane technologies, and genetic engineering. Two approaches that can use these technologies are plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of substances that can be produced from bio-based compounds can include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can also impart flame-retardant properties to bio- and petroleum-based polymers. For example, flame-retardant cross-linkers can be incorporated into polymers, and flame-retardant monomers can be polymerized to form flame-retardant polymers. Additionally, flame-retardant molecules can be blended or chemically reacted with the polymers.

Aconitic acid (propene-1,2,3-tricarboxylic acid) is one example of a bio-based compound that can have applications as a component of various polymers, resins, and molecules. Aconitic acid is an intermediate in the conversion of citrate to isocitrate during the citric acid cycle. On an industrial scale, aconitic acid is commonly obtained from fermented sugarcane extract, or synthesized from citric acid. It can be obtained from plant- and microorganism-based sources, such as those discussed above, or synthesized from petroleum-based raw materials. According to some embodiments of the present disclosure, aconitic acid is used as a precursor for flame-retardant cross-linkers. The aconitic acid-derived cross-linkers each have three functional R groups, which can bind to resins and polymers. The addition of these cross-linkers causes a resin or polymer to be flame-retardant.

Figure 1:
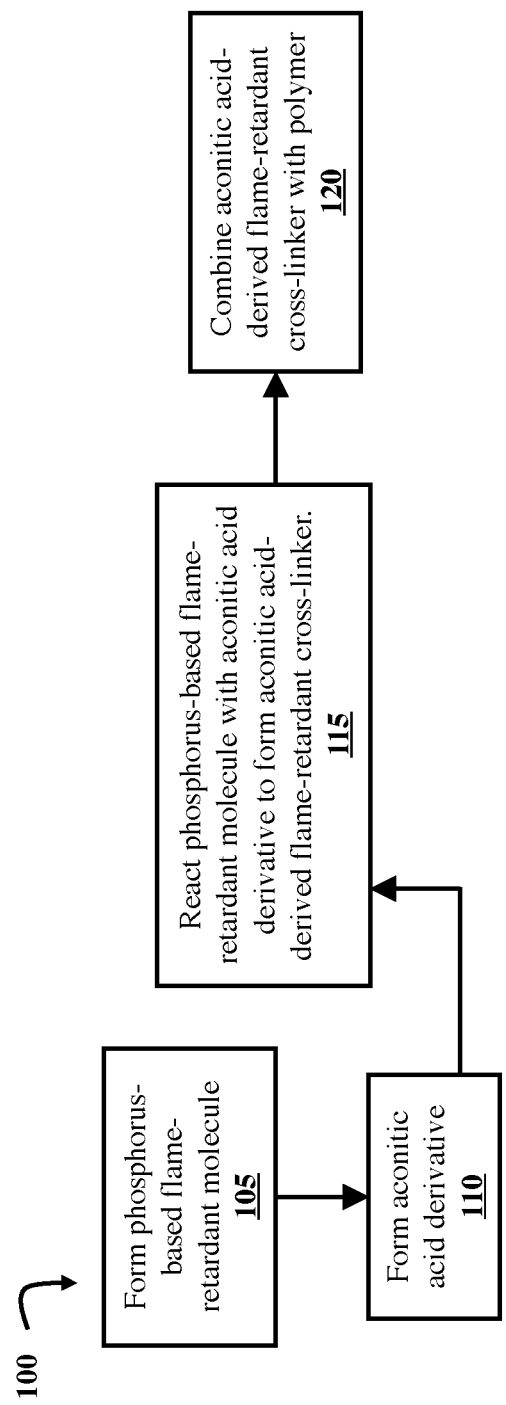
FIG. 1 is a flow diagram illustrating a process of forming a flame-retardant polymer containing an aconitic acid-derived cross-linker, according to some embodiments of the present disclosure.

FIG. 1 is a flow diagram illustrating a process 100 of forming a flame-retardant polymer containing an aconitic acid-derived cross-linker, according to some embodiments of the present disclosure. Process 100 begins with the formation of a phosphorus-based flame-retardant molecule. This is illustrated at step 105. The phosphorus-based flame-retardant molecule has either a phosphoryl or a phosphonyl moiety (collectively referred to as an FR group) with an attached R group. The R groups that are attached to the FR group can vary, as is discussed in greater detail below. The syntheses and structures of phosphorus-based flame-retardant molecules are discussed in greater detail with regard to FIGS. 2, 3A, and 3B.

Process 100 continues with the formation of an aconitic acid derivative. This is illustrated at step 110. The syntheses and structures of aconitic derivatives are discussed in greater detail with regard to FIG. 4. The aconitic acid derivative and the phosphorus-based flame-retardant molecule are chemically reacted in order to form a flame-retardant aconitic acid-derived cross-linker. This is illustrated at step 115. The structures and syntheses of flame-retardant aconitic acid-derived cross-linkers are discussed in greater detail with regard to FIGS. 1B and 5A-5L.

The identity of the flame-retardant aconitic acid-derived cross-linker formed in step 115 is determined by the aconitic acid derivative and the phosphorus-based flame-retardant molecule used in the reaction. The phosphorus-based flame-retardant molecule reacts with a hydroxyl groups on the aconitic acid derivatives to provide an FR group with an attached R group. Examples of R groups can include phenyl substituents, epoxy functional groups, allyl functional groups, propylene carbonate functional groups, hydroxyl-functionalized thioether substituents, amino-functionalized thioether substituents, carboxylic acid-functionalized thioether substituents, etc. The syntheses and structures of the flame-retardant aconitic acid-derived cross-linkers are discussed in greater detail with regard to FIGS. 5A-5L.

The aconitic acid-derived cross-linker formed in step 115 is chemically reacted with a polymer, forming a bond between the flame-retardant aconitic acid-derived cross-linkers and the polymer. This is illustrated at step 120. Examples of polymers can include epoxies, polyhydroxyurethanes, polycarbonates, polyesters, polyacrylates, polyimides, polyamides, polyureas, poly(vinyl-esters), etc. The materials for these polymers can come from petroleum-based sources, bio-based sources, or a combination of petroleum- and bio-based sources. Further, in some embodiments, the flame-retardant aconitic acid-derived cross-linkers can be used in non-polymeric applications, such as resins for varnishes and adhesives.

Figure 2:
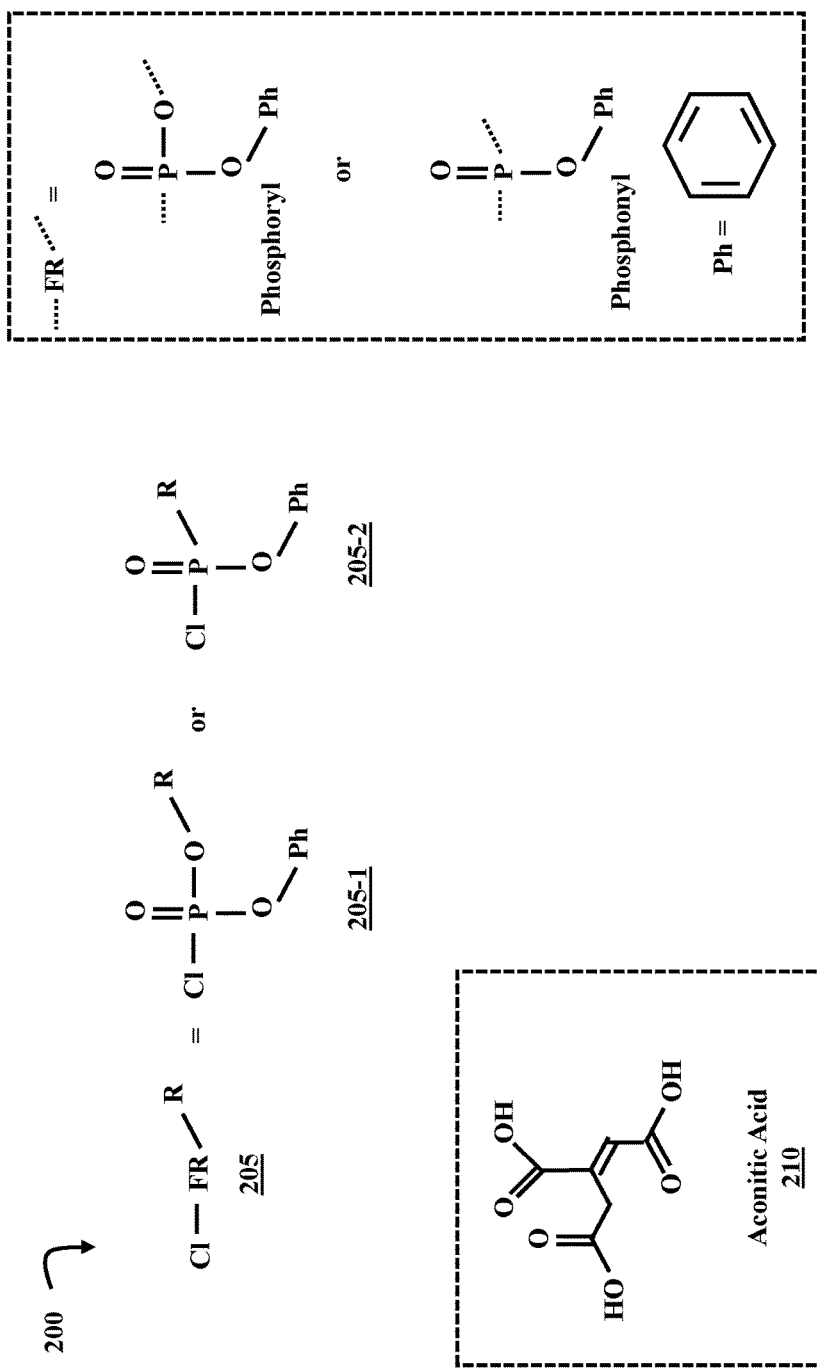
FIG. 2 is a diagrammatic representation of the molecular structures of phosphorus-based flame-retardant molecules and aconitic acid, according to some embodiments of the present disclosure.

FIG. 2 is a diagrammatic representation of the molecular structures 200 of R-substituted phosphorus-based flame-retardant molecules 205-1 and 205-2 (referred to collectively as 205) and aconitic acid 210, according to some embodiments of the present disclosure. Each phosphorus-based flame-retardant molecule 205 is either a phosphate-based flame-retardant molecule 205-1 or phosphonate-based flame-retardant molecule 205-2. Herein, phosphoryl and phosphonyl moieties are replaced by the abbreviation "FR" in order to simplify illustrations of the molecular structures.

Each phosphorus-based flame-retardant molecule 205 has a phenyl (Ph) substituent and an R functional group that can bind to a resin or polymer. In some embodiments, one or more phenyl groups on a phosphorus-based flame-retardant molecule are replaced by another alkyl substituent (e.g., ethyl, methyl, propyl, isopropyl, etc.). Prophetic syntheses of the phosphorus-based flame-retardant molecules 205 are discussed with regard to FIGS. 3A and 3B. The phosphorus-based flame-retardant molecules 205 are reacted with the aconitic acid-derived cross-linkers to form aconitic acid-derived cross-linkers. These reactions are discussed in greater detail with regard to FIGS. 4C-4F, 5A, 5D, 5G, and 5J.

Figure 3A:
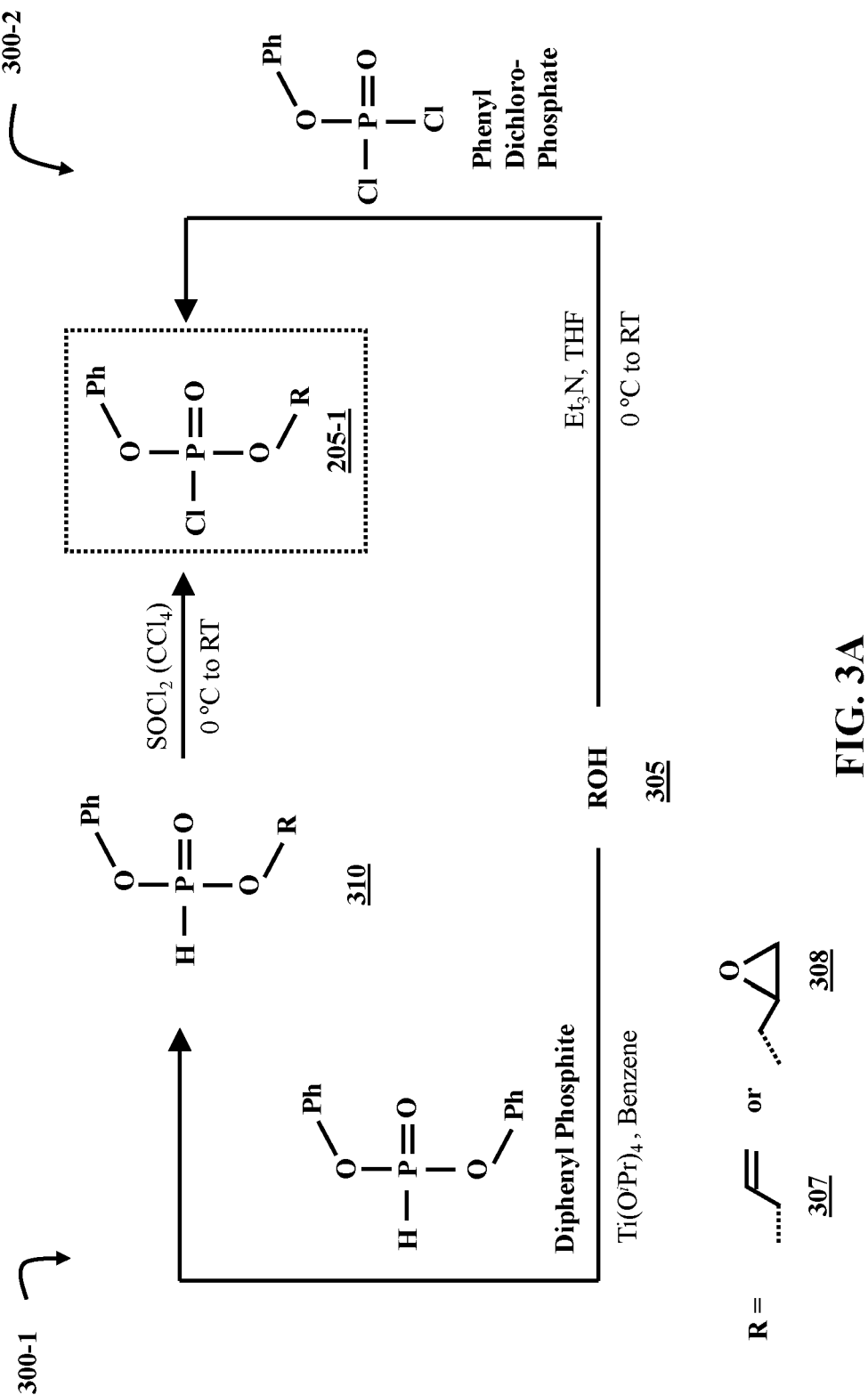
FIG. 3A is a chemical reaction diagram illustrating two processes of synthesizing the phosphate-based flame-retardant molecule, according to some embodiments of the present disclosure.

FIG. 3A is a chemical reaction diagram illustrating two processes 300-1 and 300-2 of synthesizing the phosphate-based flame-retardant molecule 205-1, according to some embodiments of the present disclosure. In both processes 300-1 and 300-2, an alcohol 305 is a starting material for the phosphate-based flame-retardant molecule 205-1. The alcohol 305 has either an allyl R group 307 or an epoxy R group 308. It should be noted that, though an allyl group 307 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 305 is reacted with diphenyl phosphonate and titanium isopropoxide ($Ti(O^iPr)_4$) in benzene to produce a precursor 310 to the phosphate-based flame-retardant molecule 205-1. In this pseudo-transesterification reaction, the precursor 310 is formed when a phenyl (Ph) substituent on diphenyl phosphite is replaced by the R group from the alcohol 305. The precursor 310 is then reacted with thionyl chloride ($SOCl_2$) and carbon tetrachloride ($CCl_4$) over a range of 0° C. to room temperature (RT, e.g., 15-25° C.), forming the phosphate-based flame-retardant molecule 205-1. In process 300-2, the alcohol 305 is reacted with phenyl dichlorophosphate in a tetrahydrofuran (THF) solution containing triethyl amine ($Et_3N$). This process is carried out over a range of 0° C. to room temperature (RT, e.g., 15-25° C.). A chloride on the phenyl dichlorophosphate is replaced by the alcohol 305, forming the phosphate-based flame-retardant molecule 205-1.

Figure 3B:
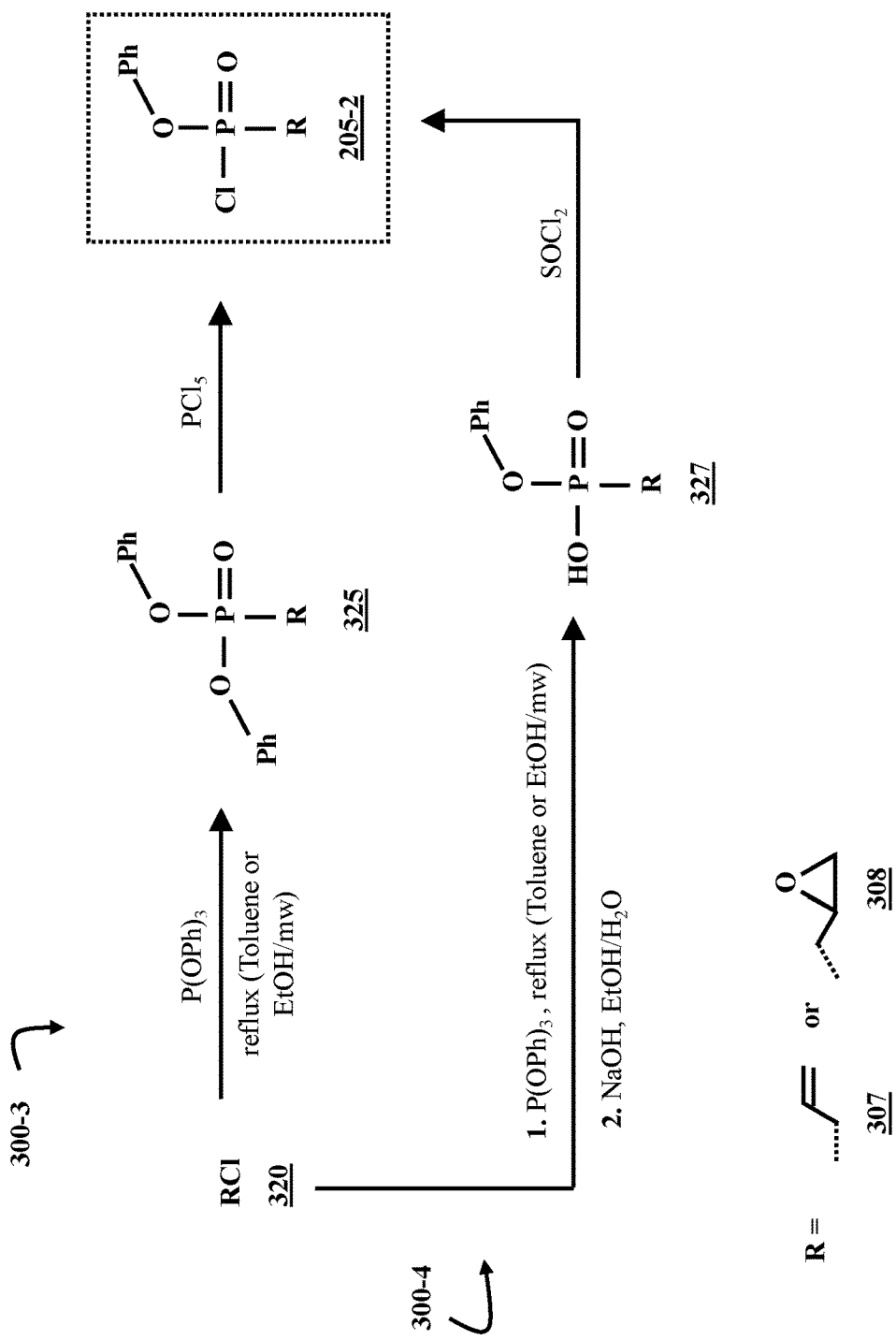
FIG. 3B is a chemical reaction diagram illustrating two processes of synthesizing the phosphonate-based flame-retardant molecule, according to some embodiments of the present disclosure.

FIG. 3B is a chemical reaction diagram illustrating two processes 300-3 and 300-4 of synthesizing the phosphonate-based flame-retardant molecule 205-2, according to some embodiments of the present disclosure. In both processes 300-3 and 300-4, an organochloride 320 is a starting material for the phosphonate-based flame-retardant molecule 205-2. The organochloride has either an allyl R group 307 or an epoxy R group 308. It should be noted that, as in the case of the alcohol 305, other organochlorides with allylic chains of varying lengths (e.g., one to twelve methylene spacer groups) could be used. Additionally, organochlorides with acrylate substituents are used in some embodiments.

In process 300-3, the organochloride 320 is reacted with triphenyl phosphite ($P(OPh)_3$). The mixture is heated, either by refluxing in toluene or microwaving (mw) in ethanol (EtOH), producing a phosphonyl ester precursor 325 to the phosphonate-based flame-retardant molecule 205-2. The phosphonyl ester precursor 325 is reacted with phosphorus pentachloride ($PCl_5$) to form the phosphonate-based flame-retardant molecule 205-2.

In process 300-4, a mixture of the organochloride 320 and triphenyl phosphite ($P(OPh)_3$) is heated, either by refluxing in toluene or microwaving (mw) in ethanol (EtOH), forming a phenylphosphinic acid precursor 327 to the phosphonate-based flame-retardant molecule 205-2. The reaction is then quenched by raising the pH of the solution. In this prophetic example, an ethanol (EtOH)/water ($H_2O$) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride ($SOCl_2$) is added to the phenylphosphinic acid precursor 327, producing the phosphonate-based flame-retardant molecule 205-2.

Figure 3C:
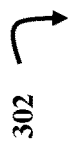
FIG. 3C is a diagrammatic representation of the molecular structures of three thiol molecules that are involved in the synthesis of aconitic acid-derived cross-linkers, according to some embodiments of the present disclosure.
Figure 3C:
Figure 3C:
Figure 3C:
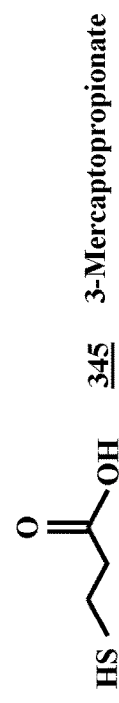

FIG. 3C is a diagrammatic representation of the molecular structures 302 of three thiol molecules that are involved in the synthesis of the aconitic acid-derived cross-linkers, according to some embodiments of the present disclosure. The three thiol molecules are 2-mercaptoethanol 335, cysteamine hydrochloride (HCl) 340, and 3-mercaptopropionate 345. Each of these thiols can provide a thioether R group in the synthesis of a thioether-linked flame-retardant aconitic acid-derived cross-linker. Details of the syntheses and structures of the thioether-linked flame-retardant aconitic acid-derived cross-linkers are discussed in greater detail with regard to FIGS. 5B, 5E, 5H, and 5K.

Figure 4:
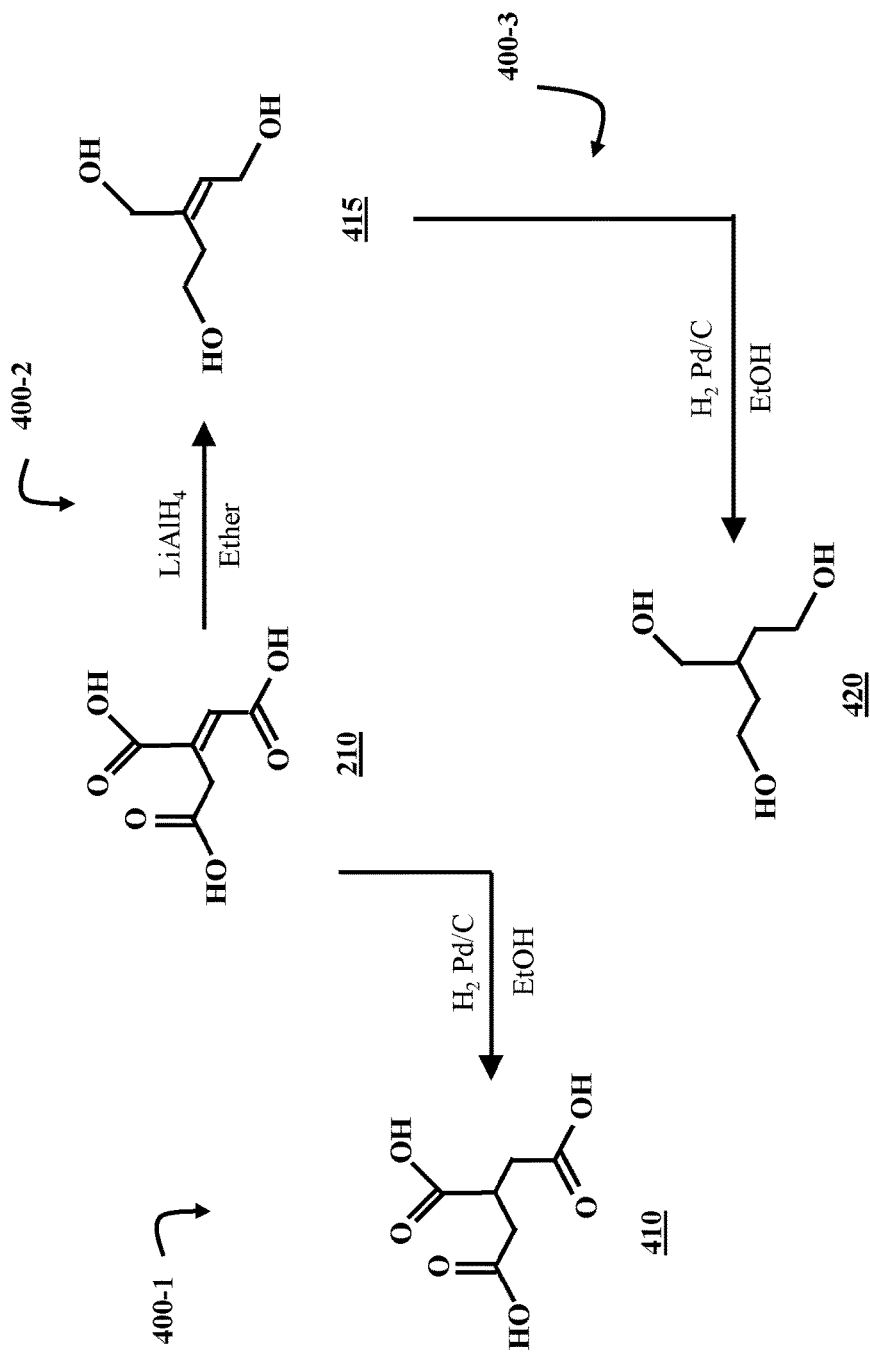
FIG. 4 is a chemical reaction diagram illustrating processes of synthesizing three derivatives of aconitic acid, according to some embodiments of the present disclosure.

FIG. 4 is a chemical reaction diagram illustrating processes 400-1, 400-2, and 400-3 of synthesizing three derivatives of aconitic acid 210, according to some embodiments of the present disclosure. The three aconitic acid derivatives are carboxysuccinic acid 410, a butenetriol 415 (2-(hydroxymethyl)-1,4-butenediol), and a butanetriol 420 (2-(hydroxymethyl)-1,4-butanediol). These aconitic acid derivatives are precursors for the flame-retardant aconitic acid-derived cross-linkers, as is described in greater detail with regard to FIGS. 5A-5L.

In process 400-1, aconitic acid 210 is reduced in an ethanol solution. The reduction is carried out with hydrogen gas ($H_2$) and a palladium on carbon (Pd/C) catalyst, and produces the aconitic acid derivative, carboxysuccinic acid 410. In process 400-2, aconitic acid 210 is reduced by lithium aluminum hydride ($LiAlH_4$) in ether ($Et_2O$), producing the butenetriol 415. In process 400-3, the butenetriol 415 is reduced under the same conditions as aconitic acid 210 in process 400-1, producing the butanetriol 420. Though FIG. 4 illustrates processes 400-1, 400-2, and 400-3 as involving the reducing agents $LiAlH_4$ and $H_2$ with Pd/C, other reducing agents can be used (e.g., sodium borohydride ($NaBH_4$), carbon monoxide (CO), iron(II) compounds, etc.). In addition, in some embodiments, carboxysuccinic acid, the butenetriol, and the butanetriol are obtained from commercial sources.

Figure 5A:
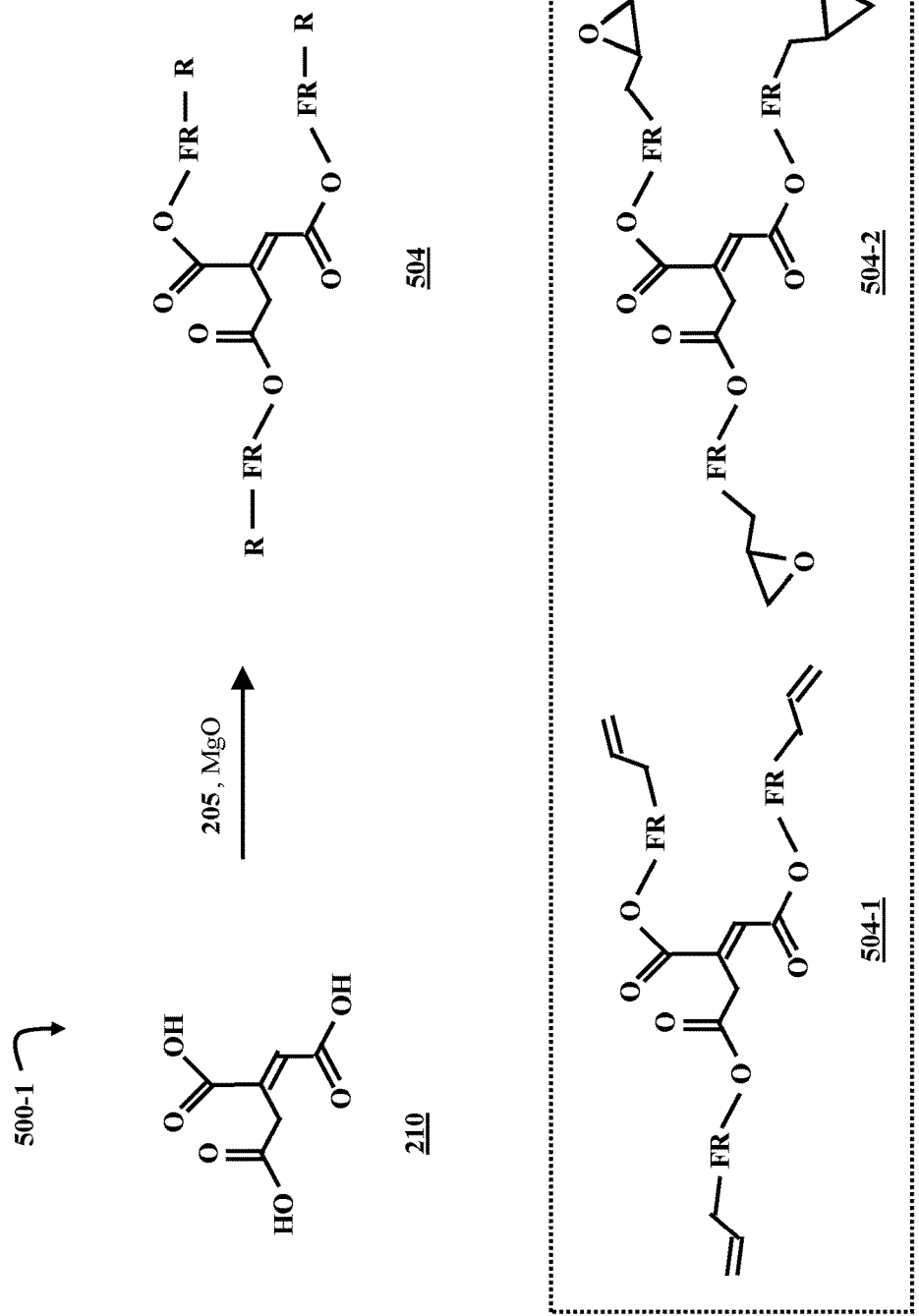
FIG. 5A is a chemical reaction diagram illustrating a process of synthesizing an allyl-functionalized and an epoxy-functionalized flame-retardant aconitic acid-derived cross-linker, according to some embodiments of the present disclosure.

FIG. 5A is a chemical reaction diagram illustrating a process 500-1 of synthesizing an allyl-functionalized and an epoxy-functionalized flame-retardant aconitic acid-derived cross-linker, according to some embodiments of the present disclosure. In this reaction, aconitic acid 210 is reacted with a phosphate-based flame-retardant molecule 205-1 or a phosphonate-based flame-retardant molecule 205-2 in the presence of magnesium oxide (MgO). The reaction between the derivative 425 and the phosphorus-based flame-retardant molecules 205 produces a functionalized flame-retardant aconitic acid-derived cross-linker 504. The identity of the functional group depends upon which phosphorus-based flame-retardant molecule 205 is used in the reaction.

If process 500-1 is carried out with a phosphorus-based flame-retardant molecule 205 having an allyl R group 307, the functionalized flame-retardant aconitic acid-derived cross-linker 504 will be an allyl-functionalized flame-retardant aconitic acid-derived cross-linker 504-1. Likewise, if process 500-1 is carried out with a phosphorus-based flame-retardant molecule 205 having an epoxy R group 308, the functionalized flame-retardant aconitic acid-derived cross-linker 504 will be an epoxy-functionalized flame-retardant aconitic acid-derived cross-linker 504-2. If process 500-1 is carried out with the phosphate-based flame-retardant molecule 205-1, the functionalized flame-retardant aconitic acid-derived cross-linker 504 will have a phosphoryl FR group, and, if the reaction is carried out with the phosphonate-based flame-retardant molecule 205-2, the functionalized flame-retardant aconitic acid-derived cross-linker 504 will have a phosphonyl FR group.

Figure 5B:
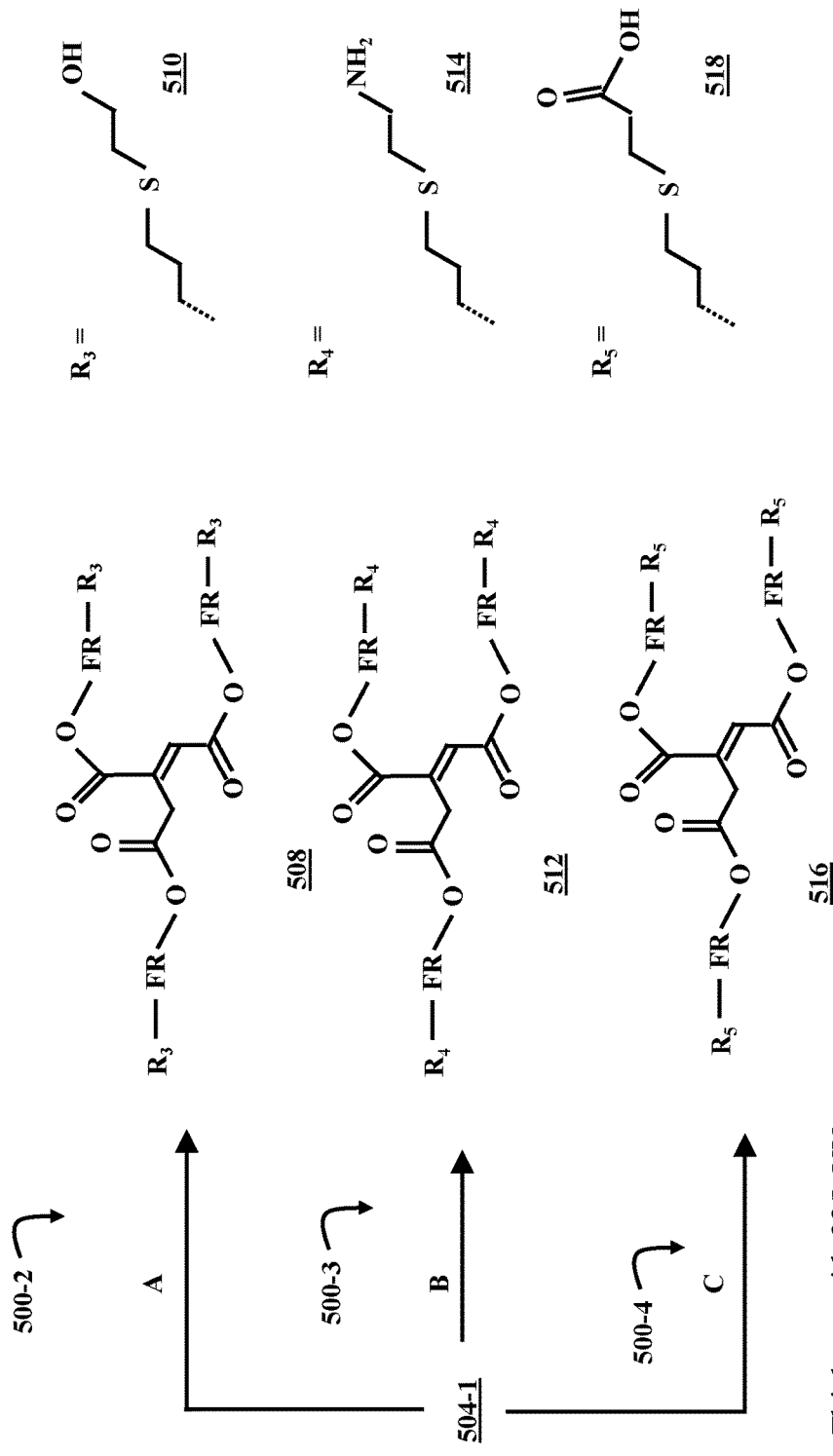
FIG. 5B is a chemical reaction diagram illustrating three processes of synthesizing thioether-linked flame-retardant aconitic acid-derived cross-linkers, according to some embodiments of the present disclosure.

FIG. 5B is a chemical reaction diagram illustrating three processes 500-2, 500-3, and 500-4 of synthesizing thioether-linked flame-retardant aconitic acid-derived cross-linkers, according to some embodiments of the present disclosure. Each process is a thiol-ene reaction between the allyl-functionalized flame-retardant aconitic acid-derived cross-linker 504-1 and a thiol molecule. The thiol molecules used in processes 500-2, 500-3, and 500-4 are 2-mercaptoethanol 335, cysteamine HCl 340, and 3-mercaptopropionate 345, respectively. The structures of these thiol molecules are illustrated in FIG. 3C.

In process 500-2, the allyl-functionalized flame-retardant aconitic acid-derived cross-linker 504-1 is reacted with 2-mercaptoethanol 335 under UV light. The resulting hydroxyl-functionalized flame-retardant aconitic acid-derived cross-linker 508 has a thioether $R_3$ group 510 that corresponds to 2-mercaptoethanol 335. In process 500-3, the allyl-functionalized flame-retardant aconitic acid-derived cross-linker 504-1 is reacted with cysteamine HCl 340 in a pH 9 methanol (MeOH) solution under UV light. The resulting amino-functionalized flame-retardant aconitic acid-derived cross-linker 512 has a thioether $R_4$ group 514 that corresponds to cysteamine HCl 340. In process 500-4, the allyl-functionalized flame-retardant aconitic acid-derived cross-linker 504-1 is reacted with 3-mercaptopropionate 345 under UV light in a methanol (MeOH) solution. The resulting carboxylic-acid functionalized flame-retardant aconitic acid-derived cross-linker 516 has a thioether $R_5$ group 518 that corresponds to 3-mercaptopropionate 345.

Figure 5C:
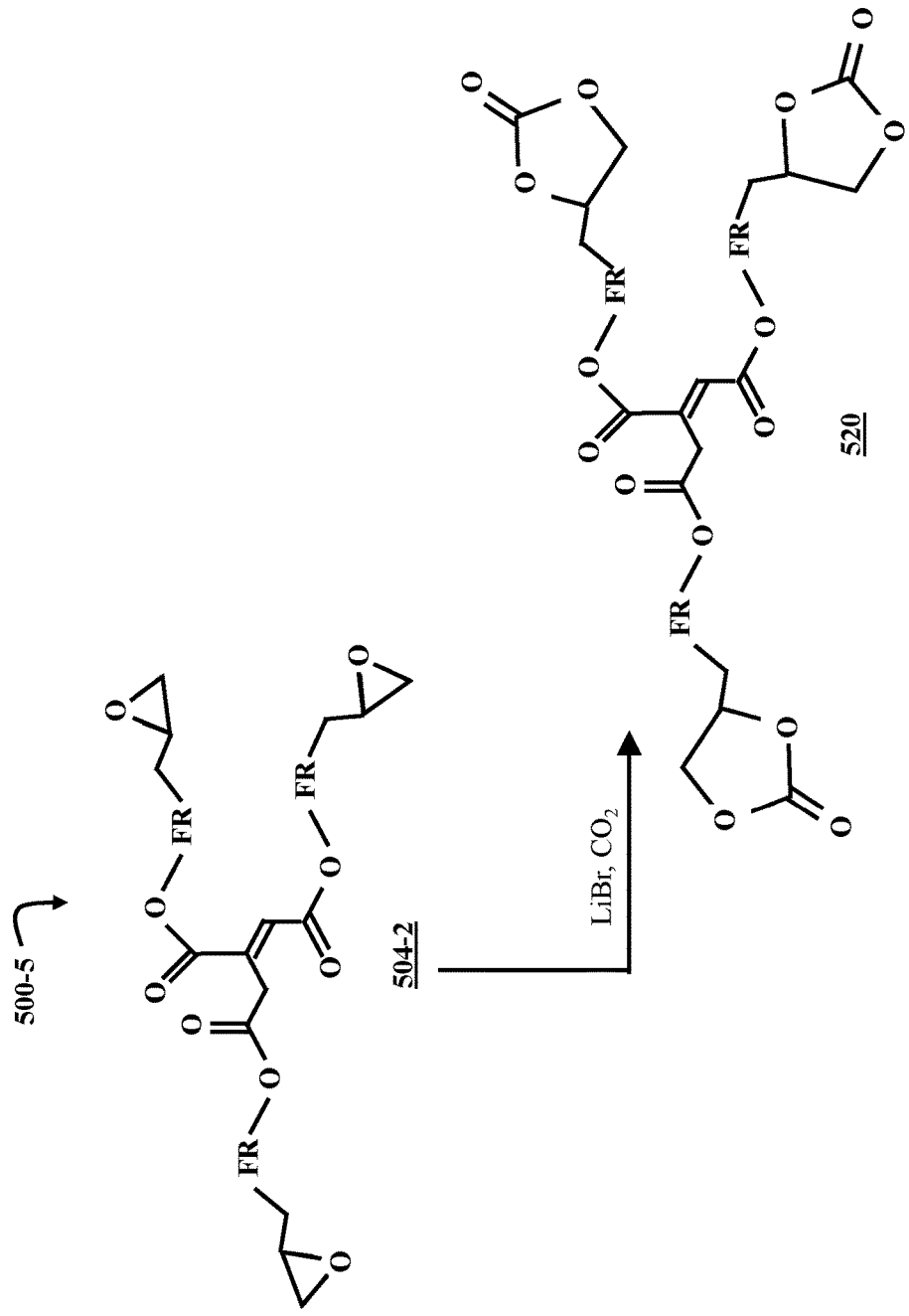
FIG. 5C is a chemical reaction diagram illustrating a process of synthesizing a propylene carbonate-functionalized flame-retardant aconitic acid-derived cross-linker, according to some embodiments of the present disclosure.

FIG. 5C is a chemical reaction diagram illustrating a process 500-5 of synthesizing a propylene carbonate-functionalized flame-retardant aconitic acid-derived cross-linker 520, according to some embodiments of the present disclosure. The epoxy-functionalized flame-retardant aconitic acid-derived cross-linker 504-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant aconitic acid-derived cross-linker 520.

Figure 5D:
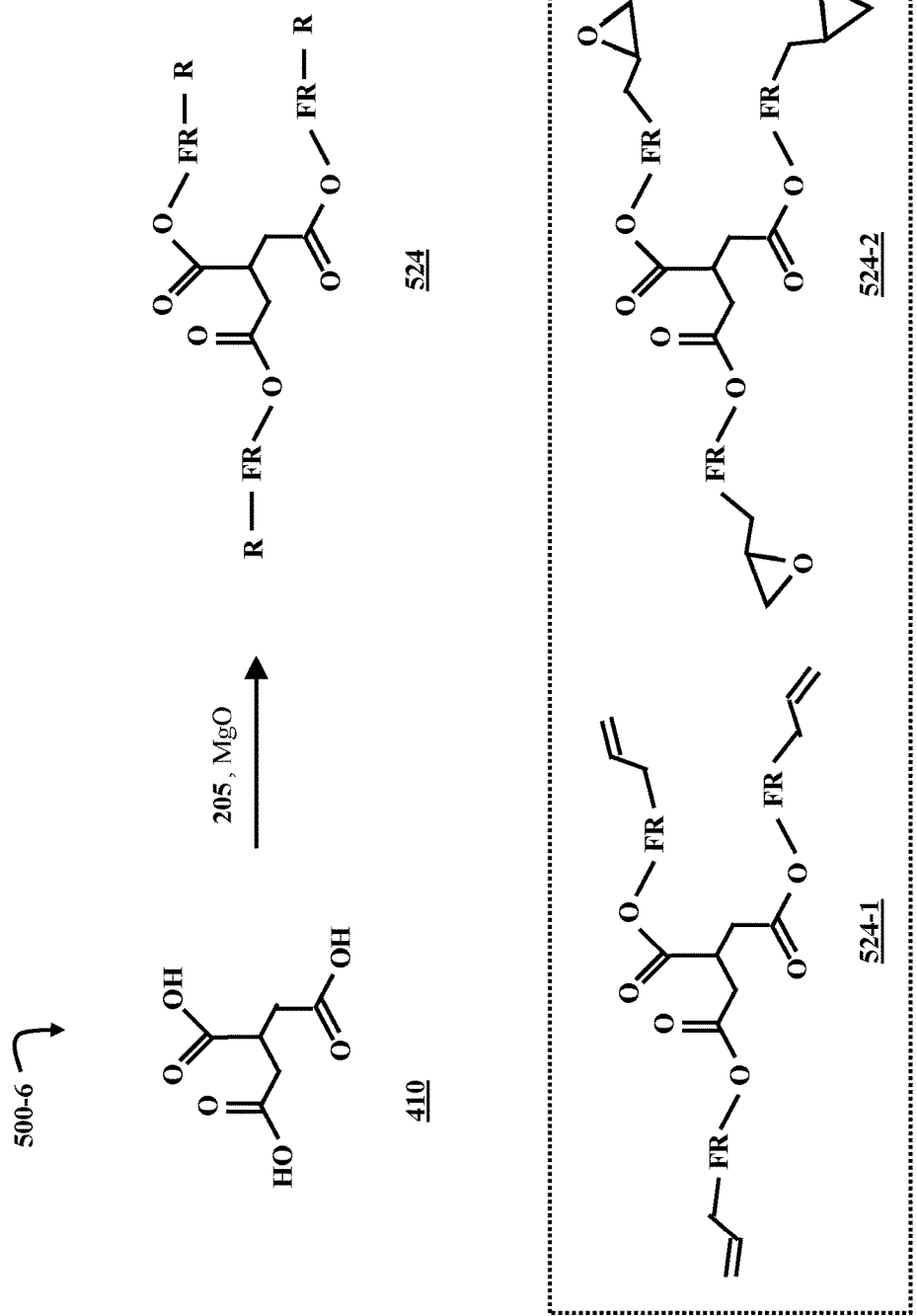
FIG. 5D is a chemical reaction diagram illustrating a process of synthesizing an allyl-functionalized and an epoxy-functionalized flame-retardant carboxysuccinic acid-derived cross-linker, according to some embodiments of the present disclosure.

FIG. 5D is a chemical reaction diagram illustrating a process 500-6 of synthesizing an allyl-functionalized and an epoxy-functionalized flame-retardant carboxysuccinic acid-derived cross-linker, according to some embodiments of the present disclosure. Carboxysuccinic acid 415 is reacted with a phosphate-based flame-retardant molecule 205-1 or a phosphonate-based flame-retardant molecule 205-2 in the presence of magnesium oxide (MgO). The reaction between the carboxysuccinic acid 415 and the phosphorus-based flame-retardant molecules 205 produces a functionalized flame-retardant carboxysuccinic acid-derived cross-linker 524. The identity of the functional group depends upon which phosphorus-based flame-retardant molecule 205 is used in the reaction.

If process 500-6 is carried out with a phosphorus-based flame-retardant molecule 205 having an allyl R group 307, the functionalized flame-retardant carboxysuccinic acid-derived cross-linker 524 will be an allyl-functionalized flame-retardant carboxysuccinic acid-derived cross-linker 524-1. Likewise, if process 500-6 is carried out with a phosphorus-based flame-retardant molecule 205 having an epoxy R group 308, the functionalized flame-retardant carboxysuccinic acid-derived cross-linker 524 will be an epoxy-functionalized flame-retardant aconitic acid-derived cross-linker 524-2. If process 500-6 is carried out with the phosphate-based flame-retardant molecule 205-1, the functionalized flame-retardant carboxysuccinic acid-derived cross-linker 524 will have a phosphoryl FR group, and, if the reaction is carried out with the phosphonate-based flame-retardant molecule 205-2, the functionalized flame-retardant carboxysuccinic acid-derived cross-linker 524 will have a phosphonyl FR group.

Figure 5E:
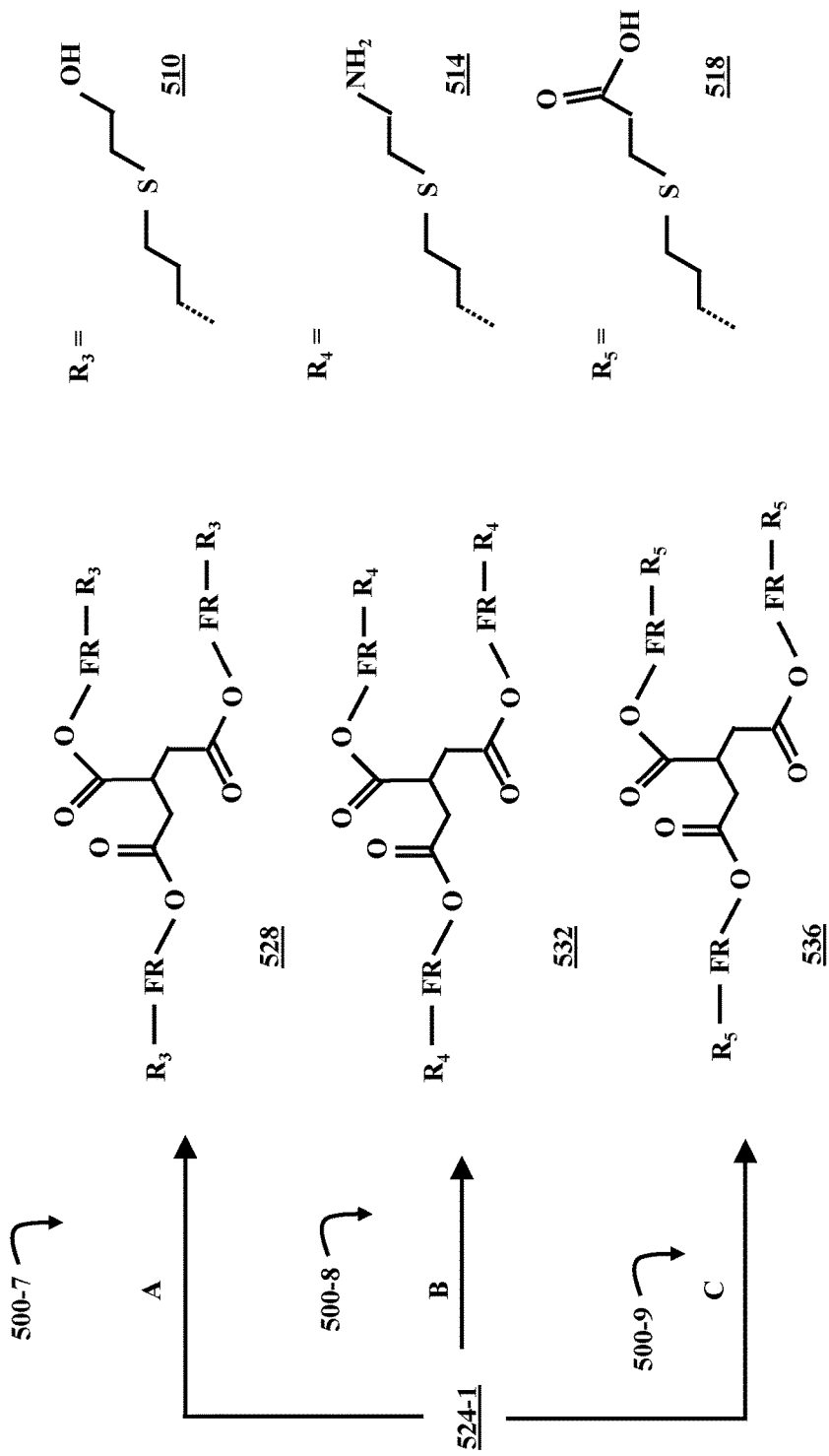
FIG. 5E is a chemical reaction diagram illustrating three processes of synthesizing thioether-linked flame-retardant carboxysuccinic acid-derived cross-linkers, according to some embodiments of the present disclosure

FIG. 5E is a chemical reaction diagram illustrating three processes 500-7, 500-8, and 500-9 of synthesizing thioether-linked flame-retardant carboxysuccinic acid-derived cross-linkers, according to some embodiments of the present disclosure. Each process is a thiol-ene reaction between the allyl-functionalized flame-retardant carboxysuccinic acid-derived cross-linker 524-1 and a thiol molecule. The thiol molecules used in processes 500-7, 500-8, and 500-9 are 2-mercaptoethanol 335, cysteamine HCl 340, and 3-mercaptopropionate 345, respectively. The structures of these thiol molecules are illustrated in FIG. 3C.

In process 500-7, the allyl-functionalized flame-retardant carboxysuccinic acid-derived cross-linker 524-1 is reacted with 2-mercaptoethanol 335 under UV light. The resulting hydroxyl-functionalized flame-retardant butenetriol-derived cross-linker 528 has a thioether $R_3$ group 510 that corresponds to 2-mercaptoethanol 335. In process 500-8, the allyl-functionalized flame-retardant carboxysuccinic acid-derived cross-linker 524-1 is reacted with cysteamine HCl 340 in a pH 9 methanol (MeOH) solution under UV light. The resulting amino-functionalized flame-retardant carboxysuccinic acid-derived cross-linker 532 has a thioether $R_4$ group 514 that corresponds to cysteamine HCl 340. In process 500-9, the allyl-functionalized flame-retardant carboxysuccinic acid-derived cross-linker 524-1 is reacted with 3-mercaptopropionate 345 under UV light in a methanol (MeOH) solution. The resulting carboxylic-acid functionalized flame-retardant carboxysuccinic acid-derived cross-linker 536 has a thioether $R_5$ group 518 that corresponds to 3-mercaptopropionate 345.

Figure 5F:
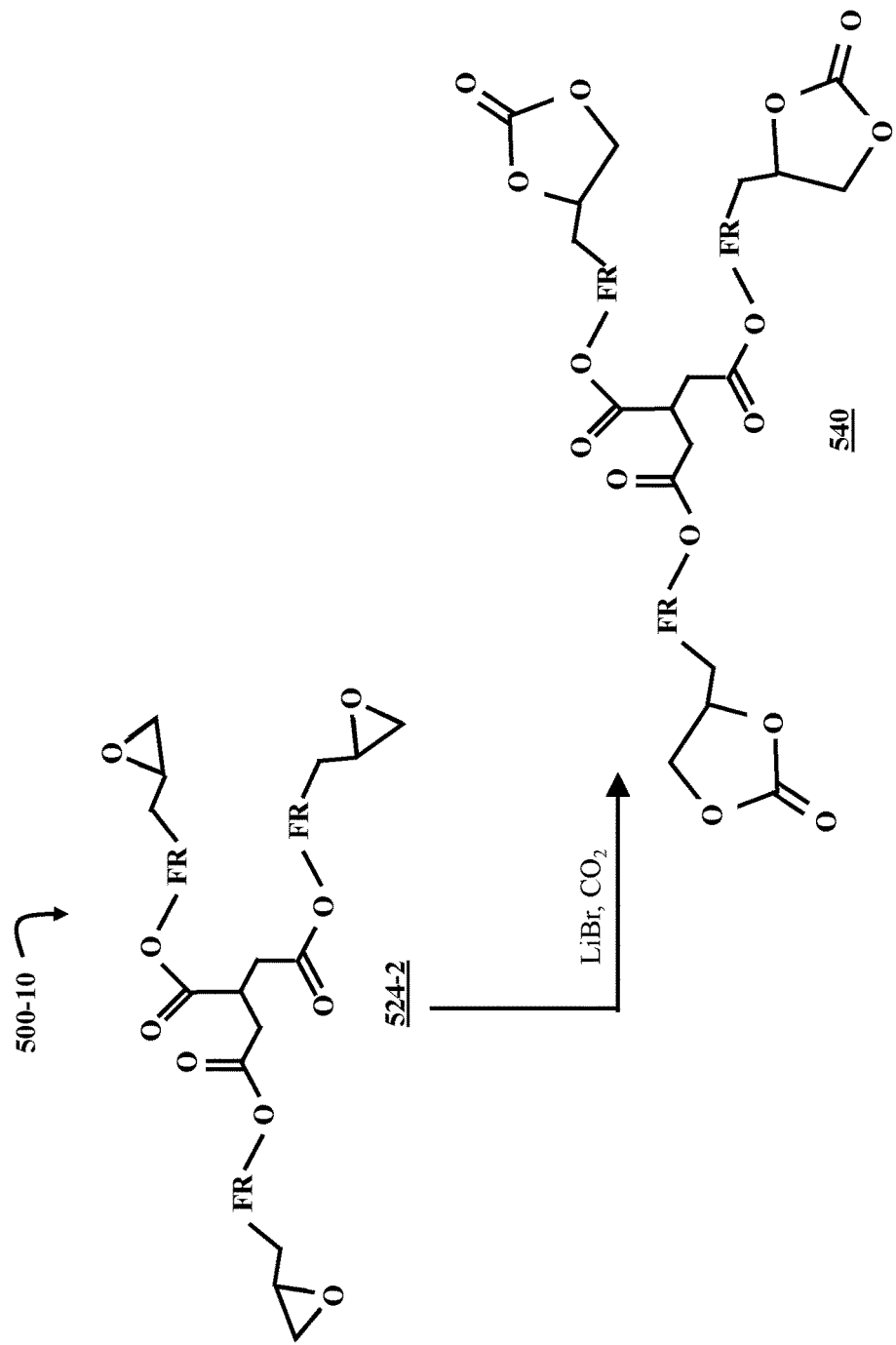
FIG. 5F is a chemical reaction diagram illustrating a process of synthesizing a propylene carbonate-functionalized flame-retardant carboxysuccinic acid-derived cross-linker, according to some embodiments of the present disclosure.

FIG. 5F is a chemical reaction diagram illustrating a process 500-10 of synthesizing a propylene carbonate-functionalized flame-retardant carboxysuccinic acid-derived cross-linker 540, according to some embodiments of the present disclosure. The epoxy-functionalized flame-retardant carboxysuccinic acid-derived cross-linker 524-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant carboxysuccinic acid-derived cross-linker 540.

Figure 5G:
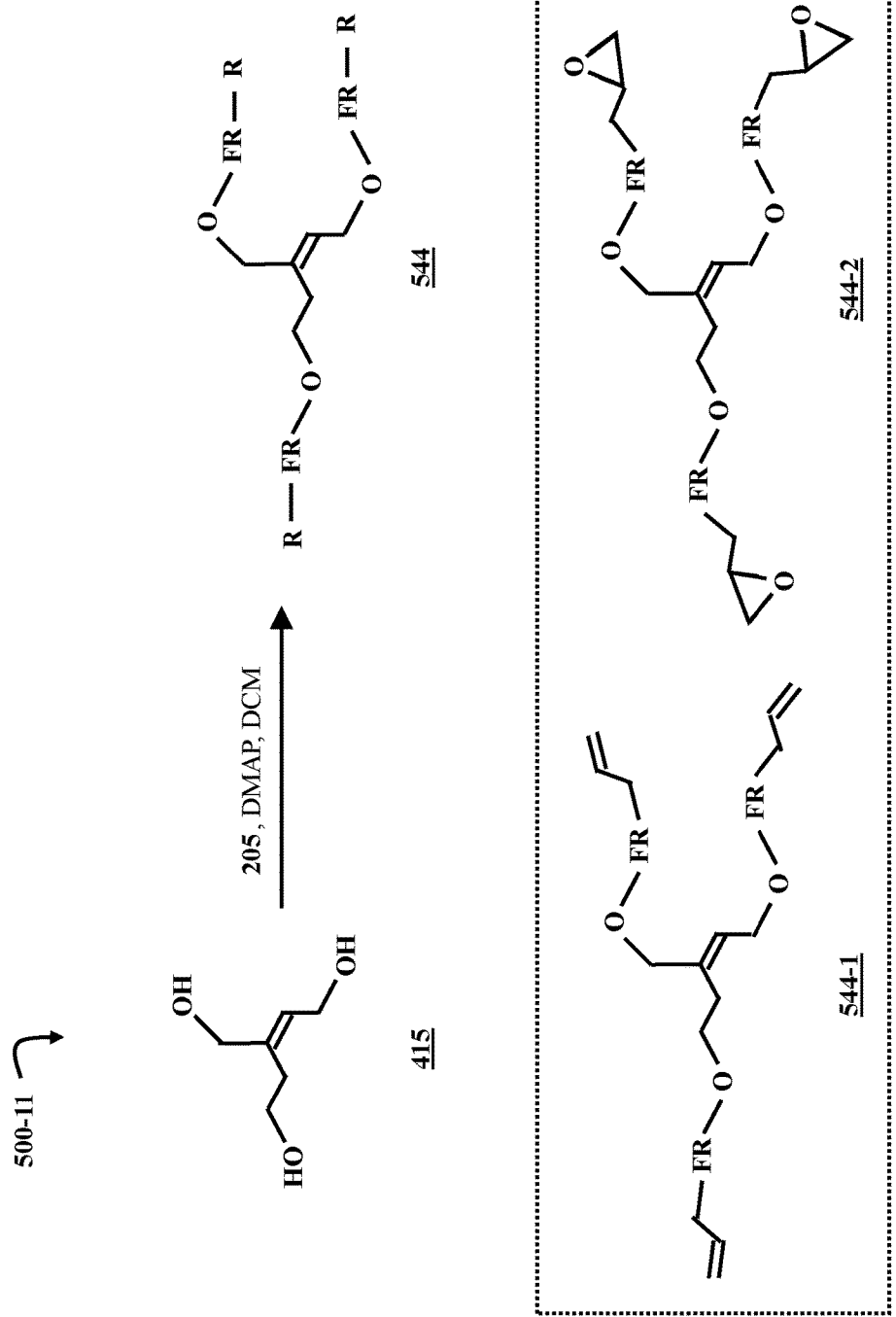
FIG. 5G is a chemical reaction diagram illustrating a process of synthesizing an allyl-functionalized and an epoxy-functionalized flame-retardant butenetriol-derived cross-linker, according to some embodiments of the present disclosure.

FIG. 5G is a chemical reaction diagram illustrating a process 500-11 of synthesizing an allyl-functionalized and an epoxy-functionalized flame-retardant butenetriol-derived cross-linker, according to some embodiments of the present disclosure. The butenetriol 415 is reacted with a phosphate-based flame-retardant molecule 205-1 or a phosphonate-based flame-retardant molecule 205-2 and catalytic dimethylaminopyridine (DMAP) in a dichloromethane (DCM) solution. The reaction between the butenetriol 415 and the phosphorus-based flame-retardant molecules 205 produces a functionalized flame-retardant butenetriol-derived cross-linker 544. The identity of the functional groups depends upon which phosphorus-based flame-retardant molecules 205 are used in the reaction.

If process 500-11 is carried out with a phosphorus-based flame-retardant molecule 205 having an allyl R group 307, the functionalized flame-retardant butenetriol-derived cross-linker 544 will be an allyl-functionalized flame-retardant butanetriol-derived cross-linker 544-1. Likewise, if process 500-11 is carried out with a phosphorus-based flame-retardant molecule 205 having an epoxy R group 308, the functionalized flame-retardant butenetriol-derived cross-linker 544 will be an epoxy-functionalized flame-retardant butenetriol-derived cross-linker 544-2. If process 500-11 is carried out with the phosphate-based flame-retardant molecule 205-1, the functionalized flame-retardant butenetriol-derived cross-linker 544 will have a phosphoryl FR group, and, if the reaction is carried out with the phosphonate-based flame-retardant molecule 205-2, the functionalized flame-retardant butenetriol-derived cross-linker 544 will have a phosphonyl FR group.

Figure 5H:
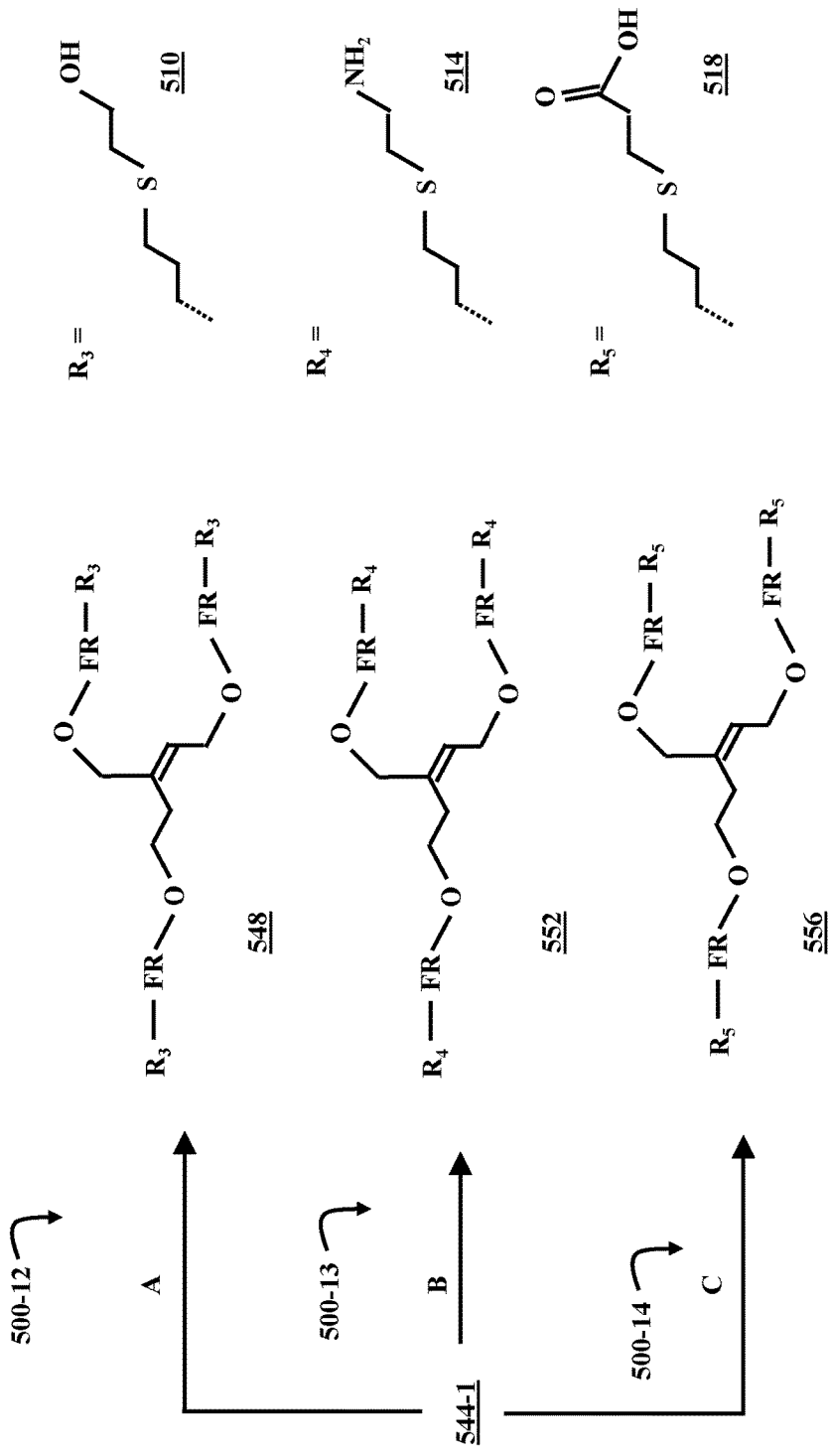
FIG. 5H is a chemical reaction diagram illustrating three processes of synthesizing thioether-linked flame-retardant butenetriol-derived cross-linkers, according to some embodiments of the present disclosure.

FIG. 5H is a chemical reaction diagram illustrating three processes 500-12, 500-13, and 500-14 of synthesizing thioether-linked flame-retardant butenetriol-derived cross-linkers, according to some embodiments of the present disclosure. Each process is a thiol-ene reaction between the allyl-functionalized flame-retardant butenetriol-derived cross-linker 544-1 and a thiol molecule. The thiol molecules used in processes 500-12, 500-13, and 500-14 are 2-mercaptoethanol 335, cysteamine HCl 340, and 3-mercaptopropionate 345, respectively. The structures of these thiol molecules are illustrated in FIG. 3C.

In process 500-12, the allyl-functionalized flame-retardant butenetriol-derived cross-linker 544-1 is reacted with 2-mercaptoethanol 335 under UV light. The resulting hydroxyl-functionalized flame-retardant butenetriol-derived cross-linker 548 has a thioether $R_3$ group 510 that corresponds to 2-mercaptoethanol 335. In process 500-13, the allyl-functionalized flame-retardant butenetriol-derived cross-linker 544-1 is reacted with cysteamine HCl 340 in a pH 9 methanol (MeOH) solution under UV light. The resulting amino-functionalized flame-retardant butenetriol-derived cross-linker 552 has a thioether $R_4$ group 514 that corresponds to cysteamine HCl 340. In process 500-14, the allyl-functionalized flame-retardant butenetriol-derived cross-linker 544-1 is reacted with 3-mercaptopropionate 345 under UV light in a methanol (MeOH) solution. The resulting carboxylic-acid functionalized flame-retardant butenetriol-derived cross-linker 556 has a thioether $R_5$ group 518 that corresponds to 3-mercaptopropionate 345.

Figure 5I:
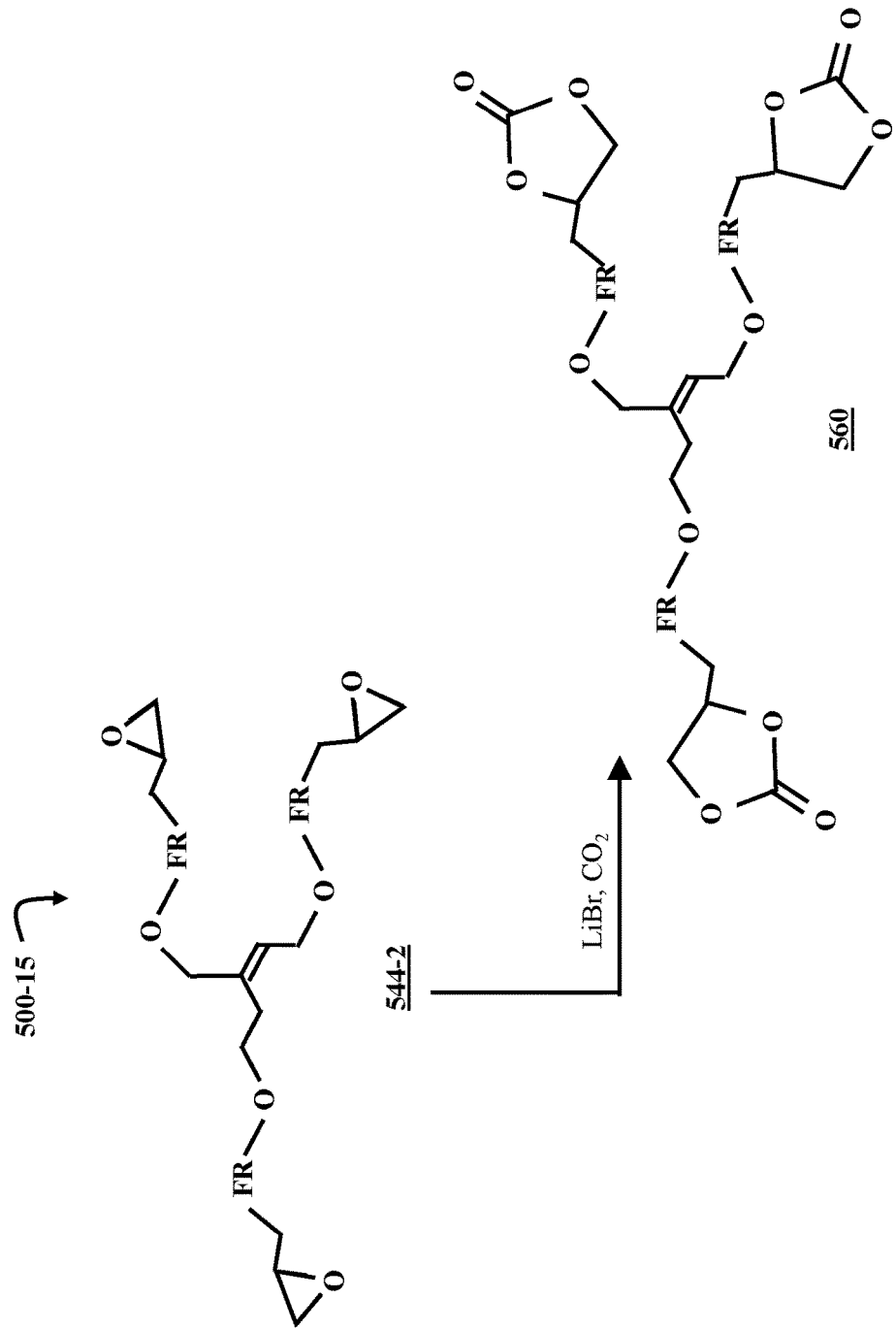
FIG. 5I is a chemical reaction diagram illustrating a process of synthesizing a propylene carbonate-functionalized flame-retardant butenetriol-derived cross-linker, according to some embodiments of the present disclosure.

FIG. 5I is a chemical reaction diagram illustrating a process 500-15 of synthesizing a propylene carbonate-functionalized flame-retardant butenetriol-derived cross-linker 560, according to some embodiments of the present disclosure. The epoxy-functionalized flame-retardant butenetriol-derived cross-linker 544-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant butenetriol-derived cross-linker 560.

Figure 5J:
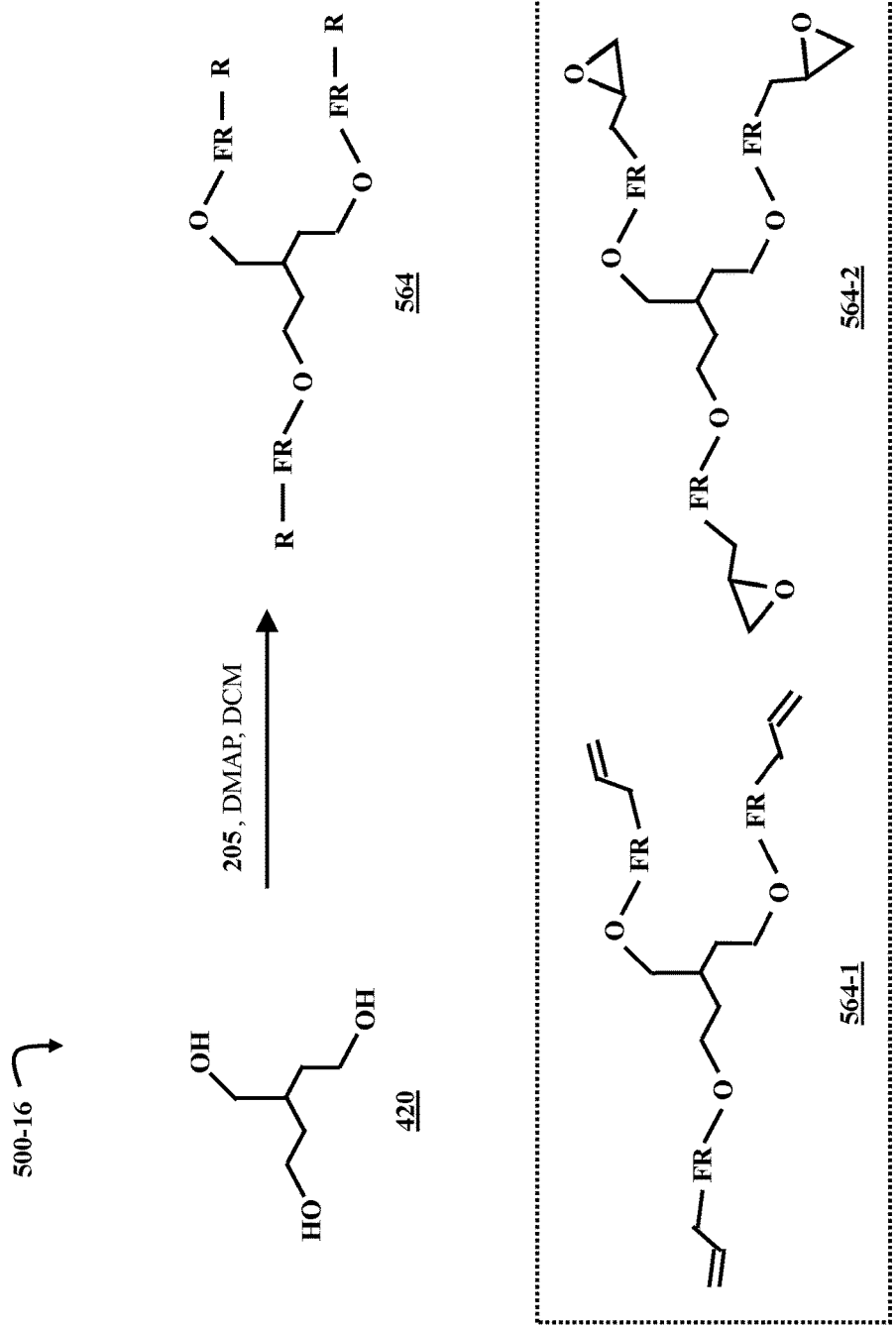
FIG. 5J is a chemical reaction diagram illustrating a process of synthesizing an allyl-functionalized and an epoxy-functionalized flame-retardant butanetriol-derived cross-linker, according to some embodiments of the present disclosure.

FIG. 5J is a chemical reaction diagram illustrating a process 500-16 of synthesizing an allyl-functionalized and an epoxy-functionalized flame-retardant butanetriol-derived cross-linker, according to some embodiments of the present disclosure. In this reaction, the butanetriol 420 is reacted with a phosphate-based flame-retardant molecule 205-1 or a phosphonate-based flame-retardant molecule 205-2 and catalytic dimethylaminopyridine (DMAP) in a dichloromethane (DCM) solution. The reaction between the butanetriol 420 and the phosphorus-based flame-retardant molecules 205 produces a functionalized flame-retardant butanetriol-derived cross-linker 564. The identity of the functional groups depend upon which phosphorus-based flame-retardant molecules 205 are used in the reaction.

If process 500-16 is carried out with a phosphorus-based flame-retardant molecule 205 having an allyl R group 307, the functionalized flame-retardant butanetriol-derived cross-linker 564 will be an allyl-functionalized flame-retardant butanetriol-derived cross-linker 564-1. Likewise, if process 500-16 is carried out with a phosphorus-based flame-retardant molecule 205 having an epoxy R group 308, the functionalized flame-retardant butanetriol-derived cross-linker 564 will be an epoxy-functionalized flame-retardant butanetriol-derived cross-linker 564-2. If process 500-16 is carried out with the phosphate-based flame-retardant molecule 205-1, the functionalized flame-retardant butanetriol-derived cross-linker 564 will have a phosphoryl FR group, and, if the reaction is carried out with the phosphonate-based flame-retardant molecule 205-2, the functionalized flame-retardant butanetriol-derived cross-linker 564 will have a phosphonyl FR group.

Figure 5K:
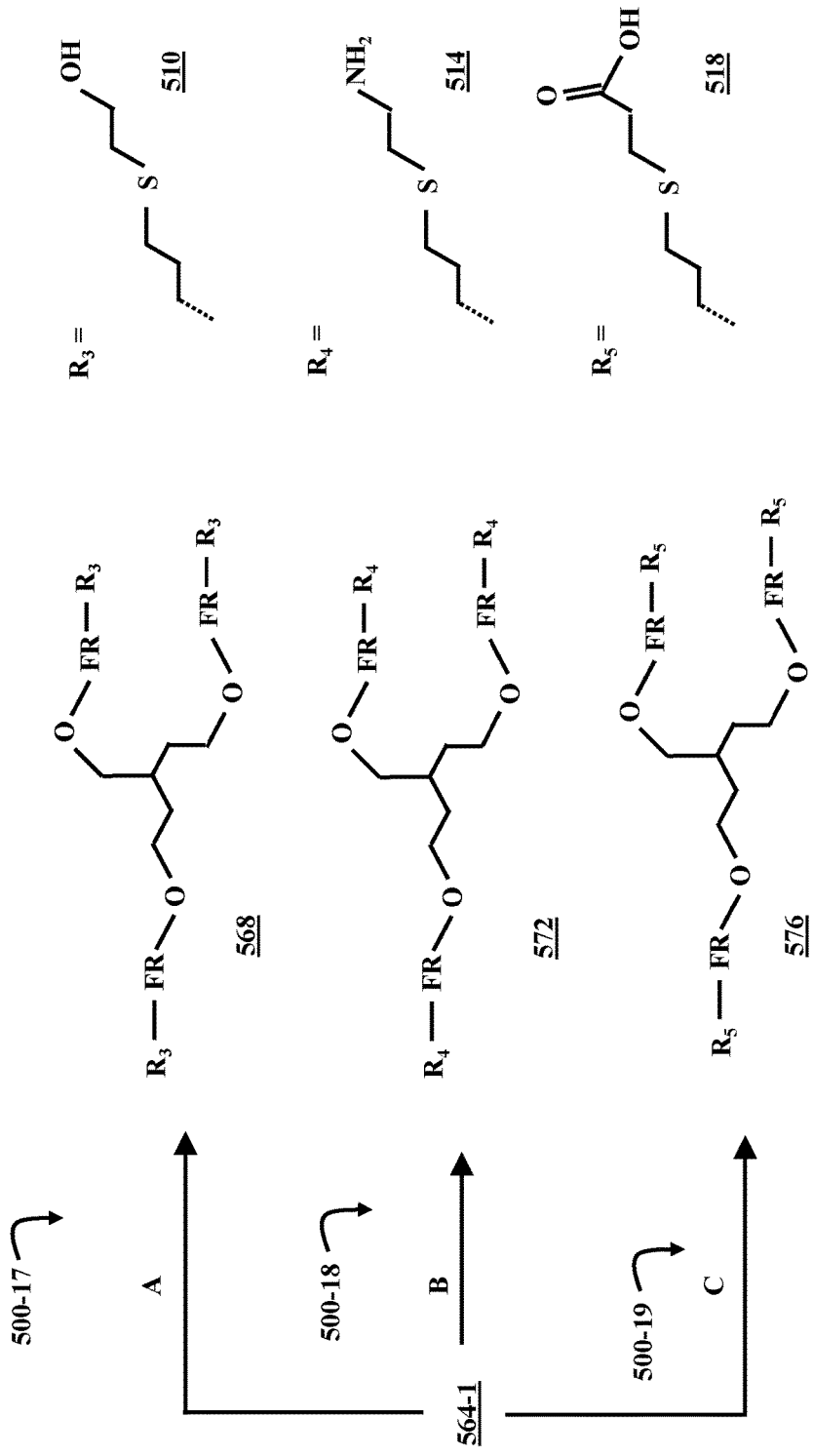
FIG. 5K is a chemical reaction diagram illustrating three processes of synthesizing thioether-linked flame-retardant butanetriol-derived cross-linkers, according to some embodiments of the present disclosure.

FIG. 5K is a chemical reaction diagram illustrating three processes 500-17, 500-18, and 500-19 of synthesizing thioether-linked flame-retardant butanetriol-derived cross-linkers, according to some embodiments of the present disclosure. Each process is a thiol-ene reaction between the allyl-functionalized flame-retardant butenetriol-derived cross-linker 564-1 and a thiol molecule. The thiol molecules used in processes 500-17, 500-18, and 500-19 are 2-mercaptoethanol 335, cysteamine HCl 340, and 3-mercaptopropionate 345, respectively. The structures of these thiol molecules are illustrated in FIG. 3C.

In process 500-17, the allyl-functionalized flame-retardant butanetriol-derived cross-linker 564-1 is reacted with 2-mercaptoethanol 335 under UV light. The resulting hydroxyl-functionalized flame-retardant butanetriol-derived cross-linker 568 has a thioether $R_3$ group 510 that corresponds to 2-mercaptoethanol 335. In process 500-18, the allyl-functionalized flame-retardant butenetriol-derived cross-linker 564-1 is reacted with cysteamine HCl 340 in a pH 9 methanol (MeOH) solution under UV light. The resulting amino-functionalized flame-retardant carboxysuccinic acid-derived cross-linker 572 has a thioether $R_4$ group 514 that corresponds to cysteamine HCl 340. In process 500-19, the allyl-functionalized flame-retardant butanetriol-derived cross-linker 564-1 is reacted with 3-mercaptopropionate 345 under UV light in a methanol (MeOH) solution. The resulting carboxylic-acid functionalized flame-retardant butanetriol-derived cross-linker 576 has a thioether $R_5$ group 518 that corresponds to 3-mercaptopropionate 345.

Figure 5L:
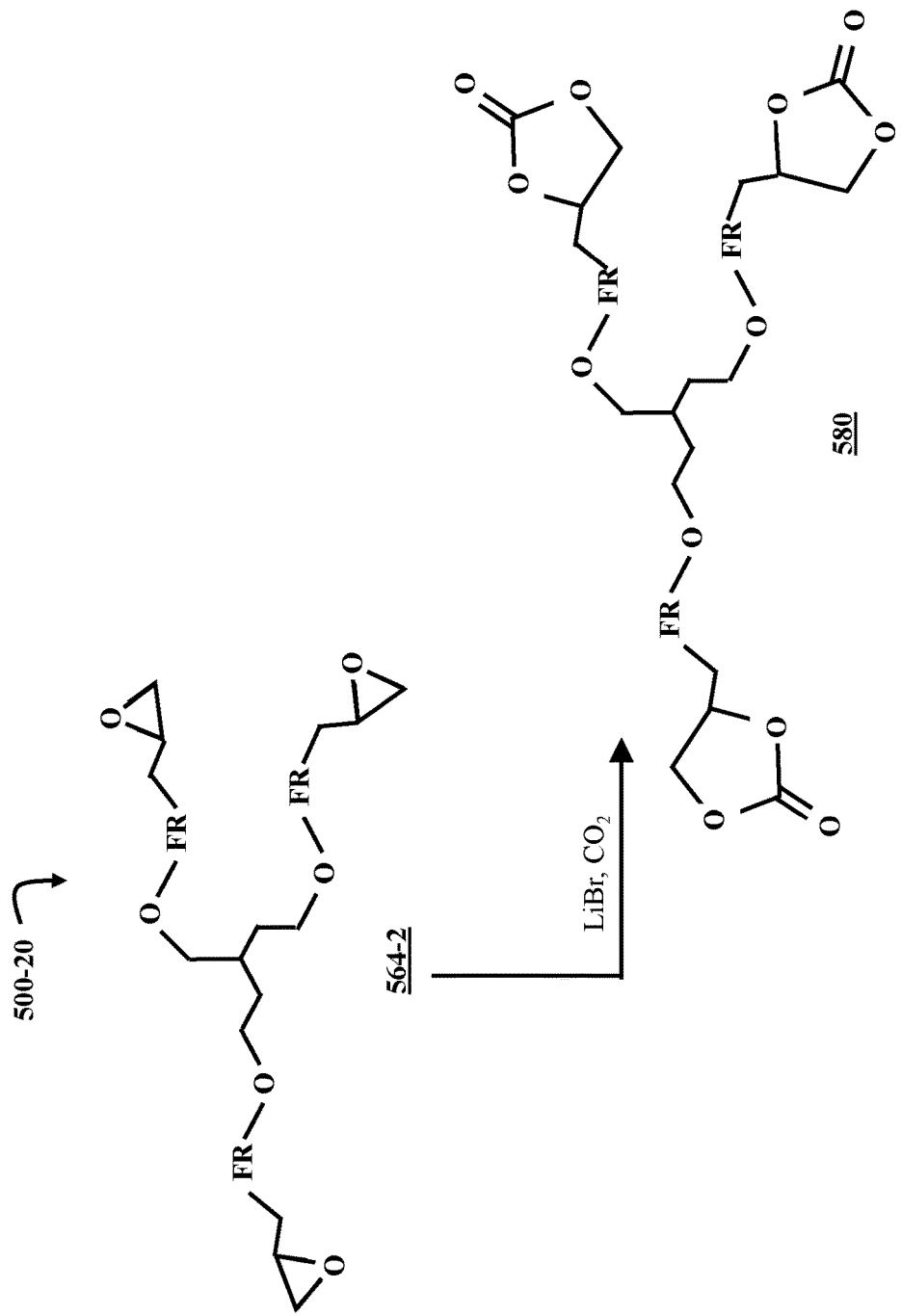
FIG. 5L is a chemical reaction diagram illustrating a process of synthesizing a propylene carbonate-functionalized flame-retardant butanetriol-derived cross-linker, according to some embodiments of the present disclosure.

FIG. 5L is a chemical reaction diagram illustrating a process 500-20 of synthesizing a propylene carbonate-functionalized flame-retardant butanetriol-derived cross-linker 580, according to some embodiments of the present disclosure. The epoxy-functionalized flame-retardant butanetriol-derived cross-linker 564-2 is combined with lithium bromide (LiBr). Carbon dioxide ($CO_2$) is added to the mixture, either by injecting it into the headspace of the reaction flask, or by bubbling it through the solution. This step yields the propylene carbonate-functionalized flame-retardant butanetriol-derived cross-linker 580.

In some embodiments, the processes 500-1, 500-6, 500-11, and 500-16 of forming aconitic acid-derived cross-linkers are carried out with a mixture of both the phosphate-based 205-1 and the phosphonate-based 205-2 flame retardant molecules. These processes are discussed in greater detail with regard to FIGS. 5A, 5D, 5G, and 5J, respectively. Reacting aconitic acid 210, carboxysuccinic acid 410, the butenetriol 415, or the butanetriol 420 with a mixture of the phosphate-205-1 and phosphonate-based 205-2 flame retardant molecules can result in aconitic acid-derived cross-linkers with both phosphoryl- and phosphonyl FR groups. However, in some instances, adding a mixture of phosphate-205-1 and phosphonate-based 205-2 flame retardant molecules can result in the production of aconitic acid-derived cross-linkers with all phosphoryl or all phosphonyl FR groups. Additionally, adding both 205-1 and 205-2 flame-retardant molecules to the reaction can yield a mixture of products that includes some combination of aconitic acid-derived cross-linkers with either all phosphoryl or all phosphonyl FR groups and aconitic acid-derived cross-linkers with both phosphoryl and phosphonyl FR groups.

The flame-retardant aconitic acid-derived cross-linkers disclosed herein bind to resins and polymers via their R functional groups. The resins can be polymerized, or used without polymerization in applications such as varnishes and adhesives. The resins and polymers are made flame-retardant by the presence of the bound aconitic acid-derived cross-linkers. The flame-retardant polymers and resins can be used in a number of applications.

One example of a polymer that can be made flame-retardant by the addition of aconitic acid-derived cross-linkers is polycarbonate-acrylonitrile butadiene styrene (PC-ABS), a plastic that is often used in electronics hardware. Flame-retardant aconitic acid-derived cross-linkers can also be incorporated into polyurethane. Polyurethane is a versatile polymer used in applications that can include acoustic dampening, cushioning, plastics, synthetic fibers, insulation, adhesives, etc. The flame-retardant aconitic acid-derived cross-linkers can also be added to adhesives such as bioadhesives, elastomers, thermoplastics, emulsions, thermosets, etc. Further, materials containing the flame-retardant aconitic acid-derived cross-linkers can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating flame-retardant aconitic acid-derived cross-linkers. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Flame-retardant aconitic acid-derived cross-linkers can be bound to the polymers in the PCB resin in order to prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. In some instances, reactions that involve multiple steps can be carried out sequentially, and, in other instances, they can be carried out in one pot. Further, in some embodiments, processes can be added or omitted while still remaining within the scope of the disclosure, as will be understood by a person of ordinary skill in the art.

What is claimed is:

1. A flame-retardant aconitic acid-derived cross-linker comprising:
   at least one phosphorus-based moiety with a formula selected from a group of formulas consisting of:

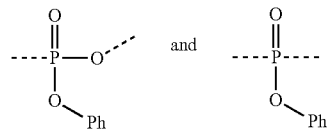

and
   at least two functional groups, wherein the at least two functional groups bind to a polymer at at least two positions.

2. The flame-retardant aconitic acid-derived cross-linker of claim 1, wherein the flame-retardant aconitic acid-derived cross-linker has a structure selected from a group consisting of molecules with formulas of:

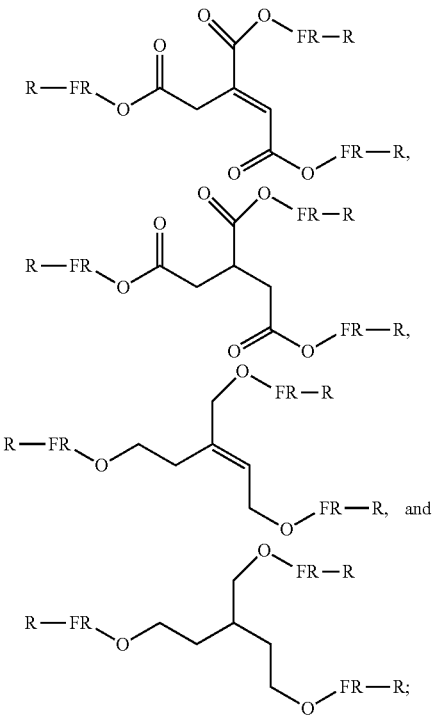

wherein FR is the at least one phosphorus-based moiety; and
wherein R is selected from a group consisting of an allyl functional group, an epoxy functional group, a propylene carbonate substituent, and a functionalized thioether substituent.

3. The flame-retardant aconitic acid-derived cross-linker of claim 2, wherein the functionalized thioether substituent is selected from a group consisting of a hydroxyl-functionalized thioether substituent, an amino-functionalized thioether substituent, and a carboxylic acid-functionalized thioether substituent.

4. The flame-retardant aconitic acid-derived cross-linker of claim 1, wherein the flame-retardant aconitic acid-derived cross-linker is synthesized from aconitic acid obtained from a bio-based source.

5. A process of forming a flame-retardant polymer, comprising:
    forming a phosphorus-based flame-retardant molecule;
    forming an aconitic acid derivative selected from a group consisting of carboxysuccinic acid, 2-(hydroxymethyl)-1,4-butenediol, and 2-(hydroxymethyl)-1,4-butanediol;
    chemically reacting the aconitic acid derivative with the phosphorus-based flame-retardant molecule to form a flame-retardant aconitic acid-derived cross-linker; and
    binding the flame-retardant aconitic acid-derived cross-linker to a polymer to form the flame-retardant polymer.

6. The of claim 5, wherein the aconitic acid derivative is synthesized from aconitic acid that has been obtained from a bio-based source.

7. The process of claim 6, wherein the bio-based source is citric acid.

8. The process of claim 5, wherein the phosphorus-based flame-retardant molecule is selected from a group consisting of phosphorus-based molecules with formulas of:

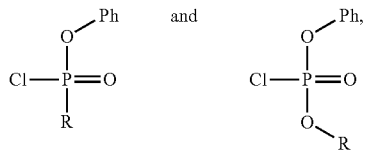

wherein R is selected from a group consisting of an allyl functional group and an epoxy functional group.

9. The process of claim 5, further comprising chemically reacting the flame-retardant aconitic acid-derived cross-linker with a thiol molecule to form a thioether-linked flame-retardant aconitic acid-derived cross-linker.

10. The process of claim 9, wherein the thiol molecule is selected from a group consisting of 2-mercaptoethanol, cysteamine hydrochloride, and 3-mercaptopropionate.

11. The process of claim 5, further comprising chemically reacting the flame-retardant aconitic acid-derived cross-linker with lithium bromide and carbon dioxide to form a propylene carbonate-functionalized flame-retardant aconitic acid-derived cross-linker.

12. An article of manufacture, comprising:
    a material containing a flame-retardant aconitic acid-derived cross-linker, the cross-linker comprising:
        at least one phosphorus-based moiety with a formula selected from a group of formulas consisting of:

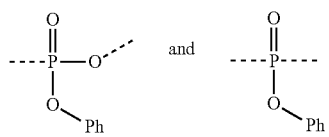

and
    at least one substituent bound to the at least one phosphorus-based moiety.

13. The article of manufacture of claim 12, wherein the flame-retardant aconitic acid-derived cross-linker is synthesized from aconitic acid obtained from a bio-based source.

14. The article of manufacture of claim 13, wherein the bio-based source is citric acid.

15. The article of manufacture of claim 12, wherein the material is selected from a group consisting of an adhesive, a resin, and a polymer.

16. The article of manufacture of claim 15, wherein the polymer is selected from a group consisting of polyurethane, an epoxy, a polyhydroxyurethane, a polycarbonate, a polyester, a polyacrylate, a polyimide, a polyamide, a polyurea, and a poly(vinyl-ester).

17. The article of manufacture of claim 12, further comprising an electronic component.

* * * * *